United States Patent [19]

Sparks

[11] Patent Number: 4,753,240

[45] Date of Patent: Jun. 28, 1988

[54] DEVICE FOR IMMOBILIZING AND APPLYING HEAT OR COLD TO A BODY JOINT

[76] Inventor: Danny R. Sparks, 518 Berwick Dr., Jackson, Miss. 39208

[21] Appl. No.: 862,778

[22] Filed: May 13, 1986

[51] Int. Cl.⁴ .......................... A61F 5/04; A61F 7/02
[52] U.S. Cl. ................................ 128/379; 128/89 R; 128/402
[58] Field of Search ............. 128/379, 380, 381, 382, 128/402, 403, 87 R, 89 R, 403

[56] References Cited

U.S. PATENT DOCUMENTS

| | | |
|---|---|---|
| 2,339,409 | 1/1944 | Joy et al. ........................ 128/379 |
| 2,769,892 | 11/1956 | Collins ............................ 128/379 |
| 3,178,559 | 4/1965 | Fogel et al. ..................... 128/399 |
| 3,748,436 | 7/1973 | Cossaboom ..................... 128/402 |
| 3,822,705 | 7/1974 | Pilotte ............................. 128/379 |
| 3,976,062 | 8/1976 | Cox ................................ 128/87 R |
| 3,999,037 | 12/1976 | Metcalf, Sr. .................... 128/379 |
| 4,033,354 | 7/1977 | De Rosa ......................... 128/379 |
| 4,042,803 | 8/1977 | Bickford ......................... 128/379 |
| 4,106,478 | 8/1978 | Higashijima ..................... 128/403 |
| 4,381,025 | 4/1983 | Schooley ......................... 128/402 |
| 4,470,417 | 9/1984 | Gruber ............................ 128/402 |
| 4,497,316 | 2/1985 | Lilla ................................ 128/87 R |
| 4,527,566 | 7/1985 | Abare .............................. 128/402 |
| 4,556,055 | 12/1985 | Bonner, Jr. ..................... 128/402 |
| 4,575,097 | 3/1986 | Brannigan ....................... 128/402 |
| 4,586,506 | 5/1986 | Nangle ............................ 128/403 |
| 4,592,358 | 6/1986 | Westplate ........................ 128/402 |

FOREIGN PATENT DOCUMENTS 162583 11/1985 European Pat. Off. ............. 128/403
1880 2/1961 United Kingdom ............. 128/87 R

OTHER PUBLICATIONS

"Braces Today", Newsletter; May 1954, Pope Foundation Inc., (p. 1).

Primary Examiner—Carl Friedman
Assistant Examiner—Michael Safavi
Attorney, Agent, or Firm—Wolf, Greenfield, Sacks

[57] ABSTRACT

An orthopedic device for immobilzing and applying heat or cold to an injured or inflamed body joint, comprising, in a preferred embodiment, a cover which may be adjustably wrapped and secured around the injured area, and within which one or more pouches, enclosing ice packs or heat packs, may be removably attached. The pouches are positionable within said cover adjacent the area or areas to be treated. Another preferred embodiment permits simultaneous treatment of an injured arm and shoulder, the device including an adjustable extension from said cover for positioning and securing a pouch against the shoulder for application of heat or cold to the shoulder.

3 Claims, 7 Drawing Sheets

DEVICE FOR IMMOBILIZING AND APPLYING HEAT OR COLD TO A BODY JOINT

FIELD OF THE INVENTION

This invention relates to an orthopedic device, and particularly to a device for immobilizing and applying heat or cold to an injured or inflamed body joint, or to post-surgical treatment of an operated joint, while permitting the patient to remain mobile during treatment.

BACKGROUND OF THE INVENTION

It has long been known that application of cold (cryotherapy) or heat to injured or inflamed joints and surrounding tissue has a therapeutic effect. It has also long been recognized that immobilization of the joint and tissue being treated is required to permit proper healing. But it is also desirable that the patient be mobile, if possible, even while undergoing treatment. The messy and cumbersome inconvenience of present cold and heat treatment techniques is often found objectionable by the patient, and frequently results in non-compliance with the prescribed treatment regimen.

Therefore, it is an object of this invention to provide a device that is adapted to immobilize a body joint while heat or cold therapy is applied by means of the device, yet presenting minimal restriction on the patient's activity.

It is another object of this invention to provide such a device that is compact, lightweight, comfortable, simple to apply, and inexpensive to manufacture.

It is still another object of this invention to provide such a device that is adjustable for patients of various body size, and is further adaptable for treatment of various injuries to a given limb of a patient.

SUMMARY OF THE INVENTION

The foregoing objects are met by the device of the present invention, which permits the simultaneous immobilization of the injured area and application of heat or cold, yet permits the patient to remain mobile during treatment. In its preferred embodiment, the present invention comprises a cover which may be wrapped and secured around the injured area, and within which one or more pouches, enclosing ice packs or heat packs, may be removably attached. The pouches are positionable within said cover adjacent the area or areas to be treated. Another preferred embodiment permits simultaneous treatment of an injured arm and shoulder, the device including an adjustable extension from said cover for positioning and securing a pouch against the shoulder for application of heat or cold to the shoulder.

DESCRIPTION OF THE PREFERRED EMBODIMENTS

Figure 1:
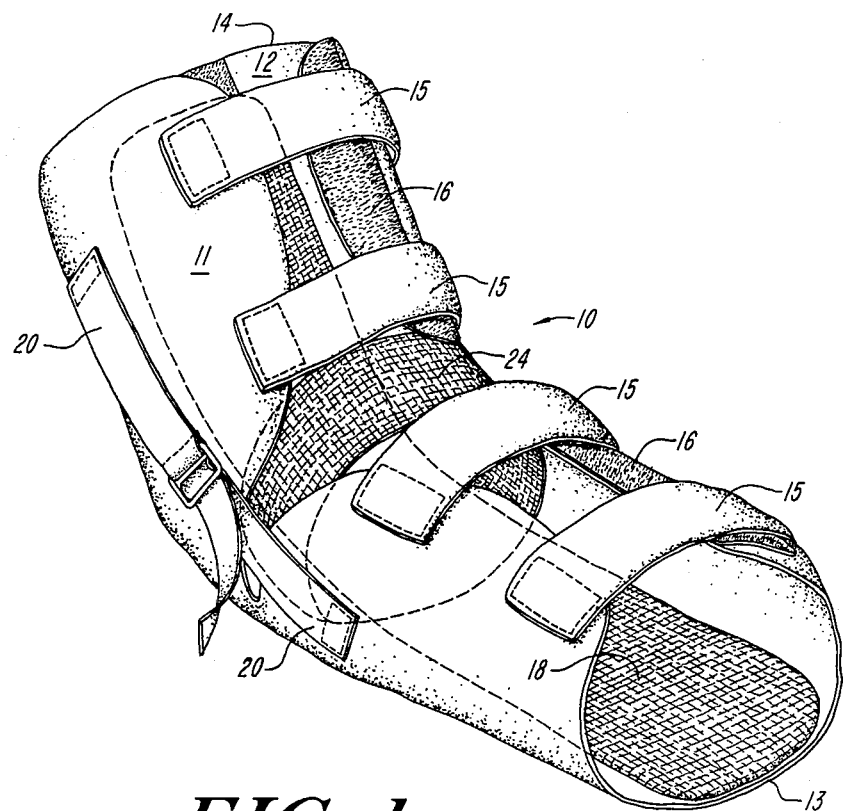
FIG. 1 is a perspective view of a preferred embodiment of the present invention arranged in the configuration utilized for immobilizing and treating an injured arm with heat or cold.

In FIG. 1 is depicted a preferred embodiment of the device 10 of the present invention, shown assembled for use in treating an injured elbow and/or forearm. Device 10 comprises an outer layer or cover 11 of flexible canvas or synthetic material, having a lower edge 13 and an upper edge 14. An inner lining 12 of soft sheepskin-like material is preferably stitched to cover 11 around its perimeter. Two strips 16 of securing material such as Velcro brand hook material are located along a side edge of cover 11. Loop material located on each of straps 15 (See FIG. 2), which straps are secured to the other side edge of cover 11, cooperates with strips 16 to enable cover 11 to be adjustably secured after the cover is wrapped around the injured arm. Two buckle straps 20, one on each side of device 10, cooperate with straps 22 to maintain the upper and lower sections of device 10 (i.e., the upper arm and lower arm portions) in proper relationship as desired, with the injured arm appropriately bent or flexed at the elbow. Closable pouches 18 and 24 are situated within the device, as more fully explained below.

Figure 2:
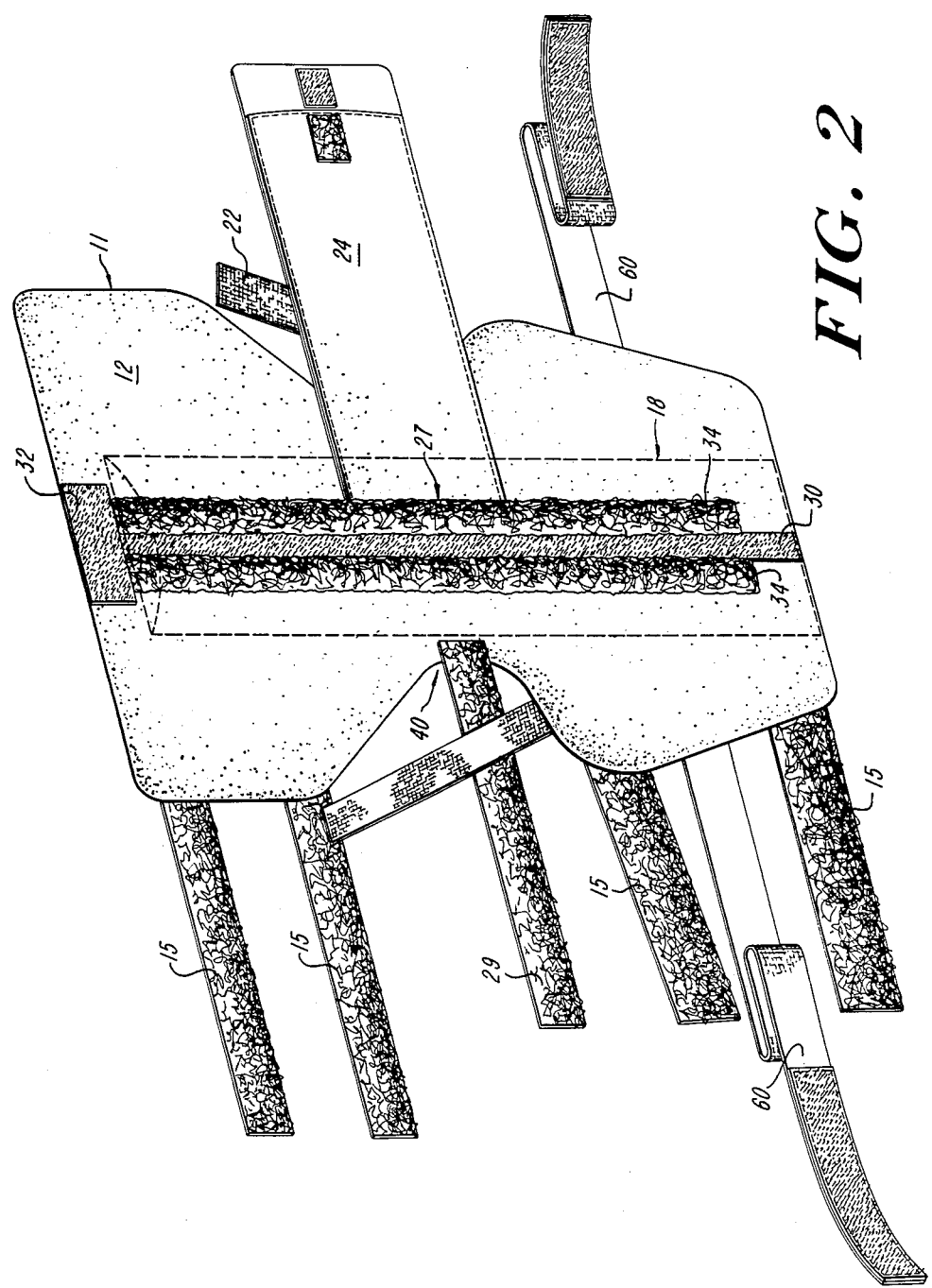
FIG. 2 is a view of the inner or patient side of the device of FIG. 1 before it is wrapped around the arm of the patient, but with one of the pouches removed.

As seen in FIG. 2, cover 11 is shaped somewhat in the form of an hourglass, the narrow waist portion 40 permitting the device to fold or bend in the region of the elbow, as seen in FIG. 1. A long strip 30 of hook-type Velcro material extends nearly the length of the device on the inner side of cover 11; a short, broad strip 32 of hook-type material is located along the top edge 14 of the device. Strip 30 cooperates with a strip of loop material 80 on pouch 18 (See FIG. 4) to secure pouch 18 within the device. Two strips 34 of soft fleeced cotton, one on each side of Velcro strip 30, serve to cushion pouch 18 when it is attached to cover 11, so that the Velcro attachment means 30 and 80 (FIG. 4), when in contact with each other, do not create a bulky, uncomfortable ridge within the device. Pouch 24, which wraps around the elbow of the patient, is secured in place by hook-type Velcro material 28 (See FIG. 3) which cooperates with loop material on the facing side of strap 29. Of course, when cover 11 is wrapped around the arm, it too serves to hold pouch 24 in place. Pouch 24 is here shown permanently affixed to the device along edge 27 opposite the pouch flap, but it too could be removably attachable.

Figure 3:
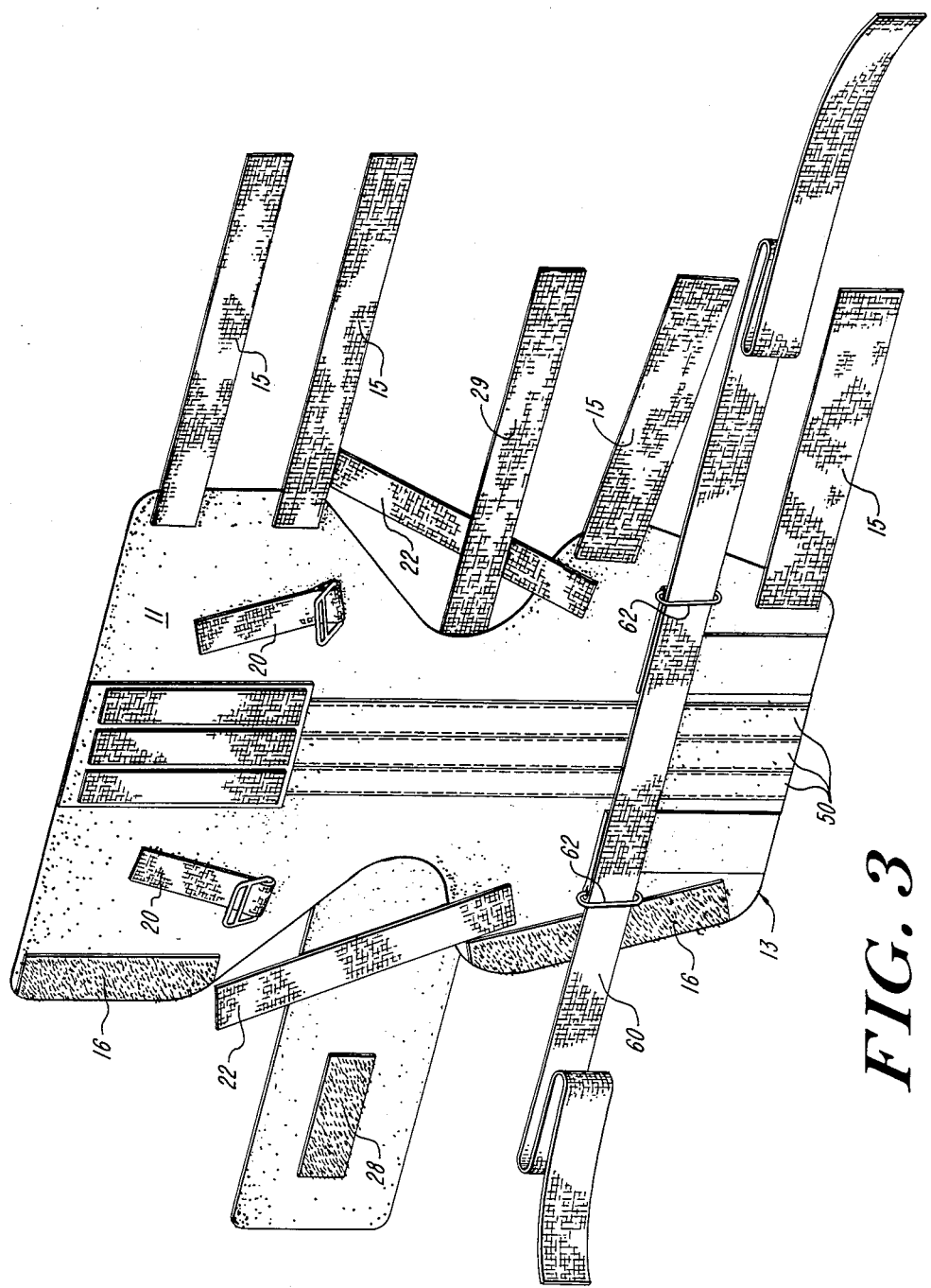
FIG. 3 is a view of the outer side of the device of FIG. 2.

Turning to FIG. 3, there is depicted the cover 11 as viewed from the outer side of the device. Elongated sleeves 50 stitched to cover 11 extend from edge 13 into the upper portion of the cover, and receive bendable metal stays (not shown), which provide rigidity and stability to the underside of the device when it is in place on the patient's arm. Shoulder strap 60 is threadable through rings 62 affixed to cover 11, and is of sufficient length to reach around the neck of the patient so as to provide support for the device and assist in immobilizing the patient's arm.

Figure 4:
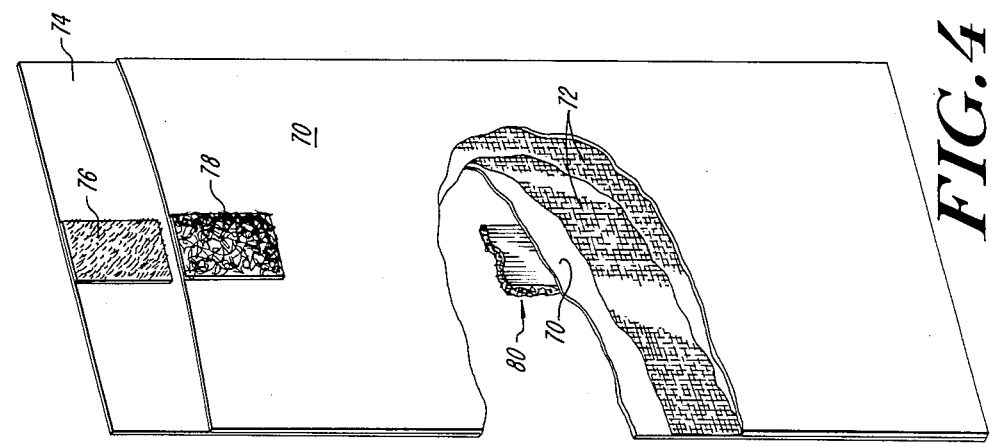
FIG. 4 is a perspective view, partly in section, of one of the detachable pouches of the present inventiion.

The construction of pouches 18 and 24 is shown in FIG. 4. Although each pouch is of different dimensions, its basic construction is the same. It comprises an outer layer 70 of canvas or other sturdy, flexible material and an inner waterproof liner 72 of rubberized cloth, plastic, or the like. Three edges of the pouch are preferably stitched to form a closable pocket, top flap 74 being foldable over the open edge of the pocket. Hook-type Velcro material 76 on flap 74 cooperates with loop material 78 to securably close the pouch. For pouch 18, a strip 80 of loop-type Velcro material is also affixed along the length of the back of the pouch, for engagement with Velcro strip 30 within cover 11.

The device of FIG. 1 is preferably utilized with the two pouches shown. However, the pouches may be of different dimensions than shown; for example, pouch 18 could be replaced by a series of smaller pouches, all or some of which may be included within the device. Furthermore, each pouch may be partly or completely filled with heat- or cold-providing material, and the pouches that are not permanently affixed may be variously positioned within the device. For cryotherapy, bags of ice or refreezable gel ice packs may be placed in the pouches. For heat therapy, re-usable gel packs may be employed.

In FIGS. 5 through 10 is depicted another preferred embodiment of the present invention. A pouch for applying heat or cold to the shoulder of the patient has been added to the device of FIG. 1. L-shaped stays 88 are receivable within sleeves 54, said sleeves being removably attachable to cover 11 by means of hook-type Velcro material on the underside of sleeves 54 (not shown) which cooperates with loop-type Velcro material 52 affixed to the upper rear portion of cover 11. The upper sections of L-shaped stays 88 are receivable within sleeves 92 formed by stitching and affixed to the upper side of pouch 90. The position of pouch 90 relative to cover 11 may be adjusted in several ways: by sliding stays 88 further into or out of sleeves 54, by removing and re-positioning sleeves 54 on loop-type Velcro material 52, and by sliding stays further into or out of sleeves 92 on pouch 90. Furthermore, pouch 90 may be adjustably shaped to conform to the shoulder of the patient by bending stays 84 described below.

Figure 5:
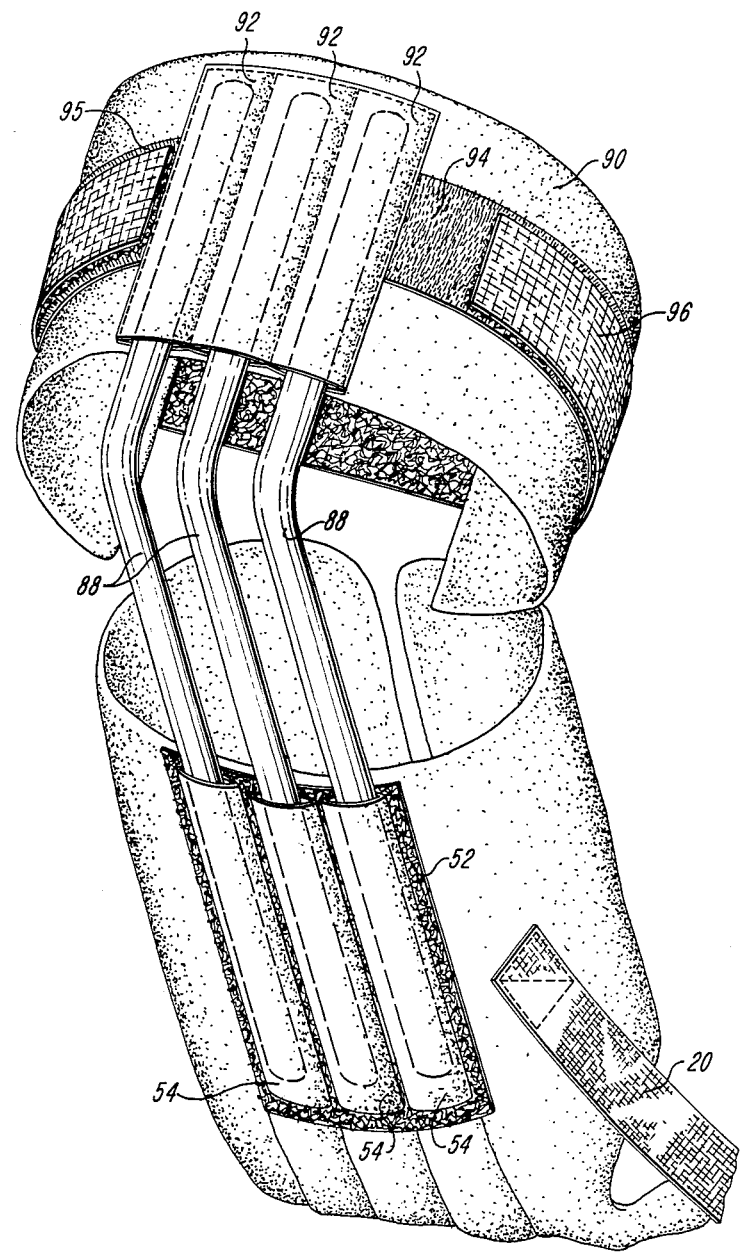
FIG. 5 is a perspective view of a second preferred embodiment of the present invention, depicting the upper portion of the device of FIGS. 1 through 4 with L-shaped stays in place for positioning and supporting a pouch for applying heat or cold to the shoulder of the patient.

In FIG. 5, pouch 90 is shown bent into a C-shape in order to wrap partly around the shoulder of the patient. Bendable metal stays 84 (shown in dotted line in FIG. 7) extend longitudinally in sleeves 89 stitched to pouch 90, and permit pouch 90 to be shaped to conform to the shoulder. Strips of hook-type Velcro material 94 and 95 on the upper side of pouch 90 may receive a strap 96 having loop-type Velcro material on one side, so that pouch 90 may be secured on the shoulder by attaching strap 96 under the the axillaors and affixing its two ends to the Velcro material 94 and 95.

Figure 7:
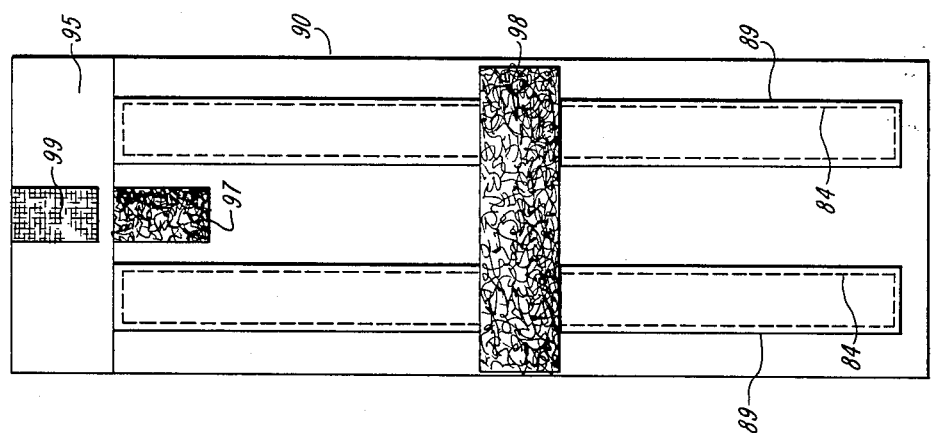
FIG. 7 is a plan view of the shoulder pouch of FIG. 6, as seen from the side that is adjacent to the shoulder.

Pouch 90 is of generally similar construction to pouches 18 and 24 and is comprised of the same layers of material. As seen in FIG. 7, flap 95 closes the pouch, and is securable to the body of the pouch by the cooperation of hook-type Velcro material 99 on flap 95, and loop-type Velcro material 97 at the open edge of the pocket area. A strip of loop-type Velcro material 98 permits that attachment of an upper arm pouch described below.

Figure 6:
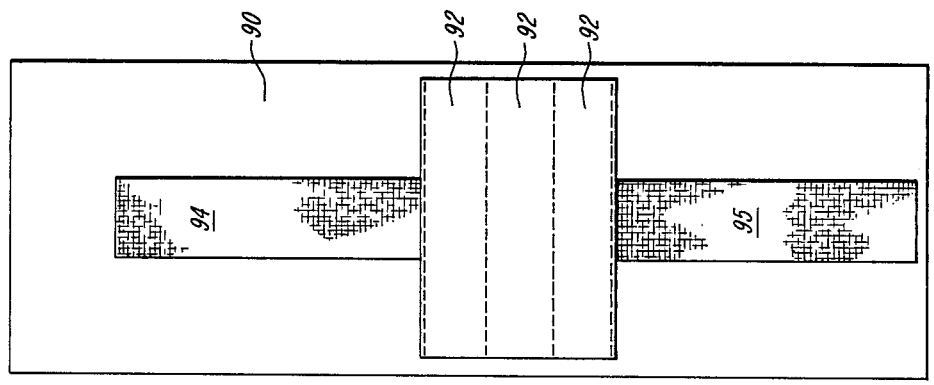
FIG. 6 is a plan view of the shoulder pouch of FIG. 5 in its unbent condition, as seen from the side positioned away from the shoulder.
Figure 8:
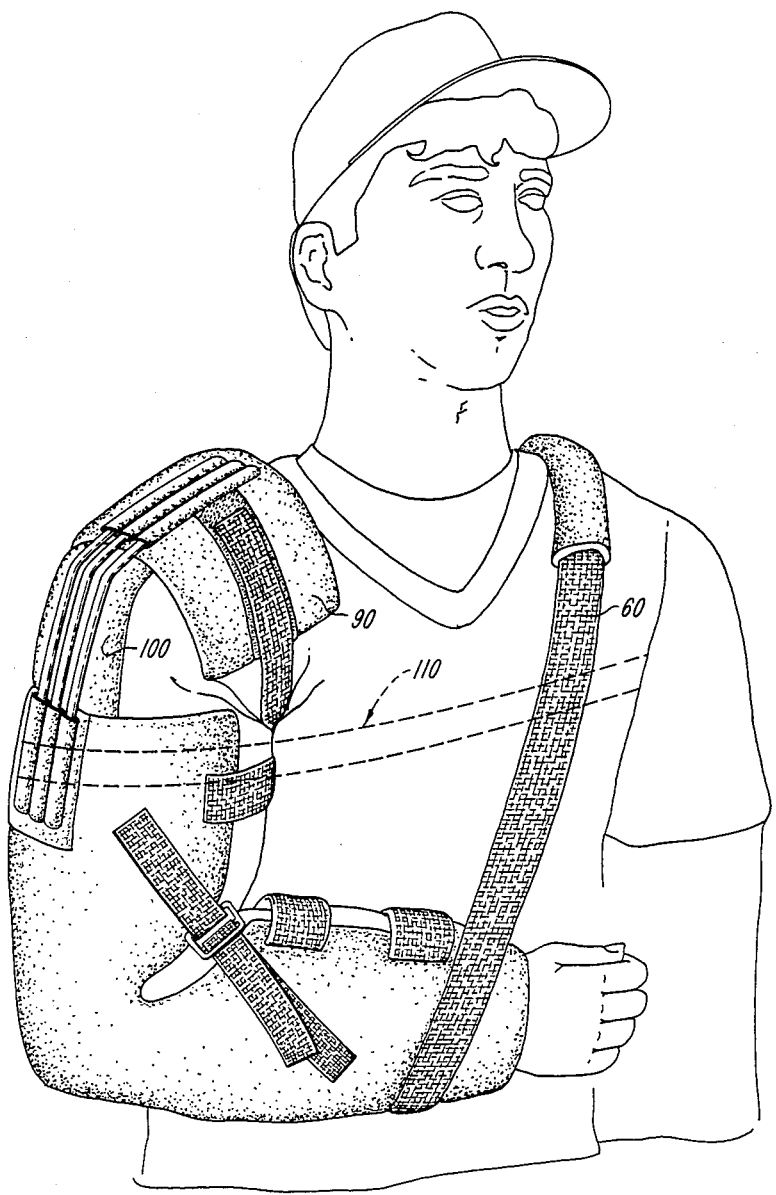
FIG. 8 is a perspective view illustrating the device of FIGS. 5 through 7 applied to a patient's arm and shoulder, with the addition of a pouch applied to the upper arm and attached at opposite ends to the cover and the shoulder pouch.

Turning to FIG. 8, the device of FIGS. 5 through 7 is illustrated as applied to a patient, but with the addition of an upper arm pouch 100. Strap 110 (shown in dotted line) is wrapped around the chest of the patient and serves to hold the shoulder extension firmly against the shoulder area.

Figure 9:
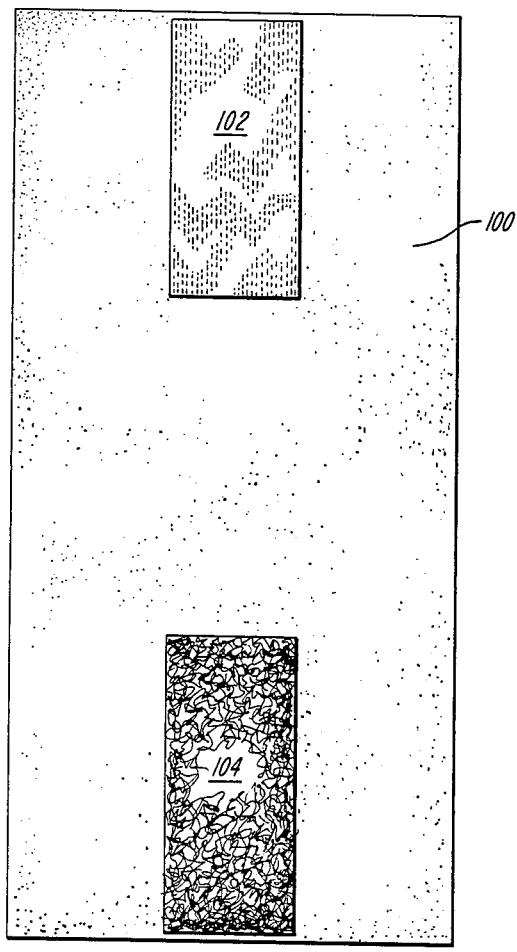
FIG. 9 is a plan view of the upper arm pouch of FIG. 8, as seen from the side away from the shoulder.

FIG. 9 depicts the outer side of upper armors pouch 100, which is of the same internal construction as pouches 18 and 24 (FIG. 4). A strip of hook-type Velcro material 102 affixed to pouch 100 cooperates with corresponding strip 98 of loop-type material (FIG. 7) to detachably secure upper arm pouch 100 to the underside of shoulder pouch 90. A strip of loop-type Velcro material 104 affixed to pouch 100 cooperates with strip 32 of hook-type material at the upper edge 14 on the inside of cover 11 to detachably secure upper arm pouch 100 to cover 11. As seen in FIG. 8, upper arm pouch 100 serves to provide heat or cold to the area of the arm generally between the top of cover 11 and the edge of shoulder pouch 90. Its position in relation to cover 11 and shoulder pouch 90 may be adjusted by appropriate placement of the Velcro strips 102 and 104 on corresponding Velcro strips 98 and 32, respectively.

The device of the present invention has proven to be effective in post-surgical treatment and in treating acute musculoskeletal injuries including joint sprains, muscle strains, inflammations, and contusions. It is also effective in treating athletic injuries resulting from repetitive stress, such as inflammation of the shoulder and elbow experienced by baseball pitchers, tennis elbow, and inflammation of the ankle and knee encountered by runners and dancers.

Heat therapy utilizing the present invention is beneficial in cases of chronic inflammatory conditions of the musculoskeletal system such as rheumatoid arthritis, chronic myositis, bursitis, and osteoarthritis.

It will be evident to those of ordinary skill in the art that the present invention is applicable not only to treatment of an injured arm or shoulder, but to injuries to any limb or joint. Based upon the foregoing disclosure, one could readily construct a device that would provide cold or heat treatment by means of removable, positionable, re-usable pouches in an adjustable immobilizing cover secured around, for example, an injured knee or ankle. The preceding disclosure is therefore not intended to limit the present invention to the preferred embodiments shown and described.

What is claimed is:

1. An orthopedic device for immobilizing and applying heat or cold to the arm and shoulder of a patient, comprising:

a flexible cover adaptable for wrapping at least partly around said arm, said cover having an inner side and an outer side;

means for adjustably securing said cover to said arm;

first securement means affixed to the inner side of said cover;

a first pouch for receipt of cold or heat providing material, said pouch being detachably securable to said first securement means within said cover for contacting said patient in a selected area of the arm so that the heat or cold may flow to the selected area when the cover is affixed to the patient;

a shoulder pouch for receipt of heat or cold providing material;

means for positioning and supporting said shoulder pouch with respect to said cover in contact with the shoulder of said arm so that the heat or cold may flow to the shoulder;

second securement means affixed to said shoulder pouch; and an upper arm pouch for receipt of heat or cold providing material, said upper arm pouch having a first end and a second end, and said upper arm pouch being adjustably secured at said first end to said first securement means, and at said second end to said second securement means, for providing heat or cold to the upper arm and lower shoulder area.

2. An orthopedic device for immobilizing and applying heat or cold to the arm and shoulder of a patient, comprising:

a flexible cover adaptable for wrapping at least partly around said arm, said cover having an inner side and an outer side;

means for adjustably securing said cover to said arm;

securement means affixed to the inner side of said cover;

a first pouch for receipt of cold or heat providing material, said pouch being detachably securable to said securement means, for contacting said patient in a selected area of the arm so that the heat or cold may flow to the selected area when the cover is affixed to the patient;

a shoulder pouch for receipt of heat or cold providing material;

means for positioning and supporting said shoulder pouch with respect to said cover in contact with the shoulder of said arm so that the heat or cold may flow to the shoulder, said positioning and supporting means including bendable stay means located within said shoulder pouch to permit the shoulder pouch to be shaped to conform to the contours of the shoulder, and further including means for adjusting the position of said shoulder pouch with respect to said cover, said adjusting means comprising an L-shaped stay having a first and second end, the first end being slidable receivable within a first sleeve affixed to said cover, and the second end being slidably receivable in as second sleeve affixed to said shoulder pouch.

3. The device of claim 2 further comprising means for detachably securing said first sleeve to said cover for adjusting the position of said sleeve and thus said L-shaped stay with respect to said cover.

* * * * *